United States Patent [19]

Epinette

[11] Patent Number: 4,743,261
[45] Date of Patent: May 10, 1988

[54] TIBIAL COMPONENT FOR UNICOMPARTMENTAL KNEE PROSTHESIS FOR A CEMENTNESS IMPLANTATION

[76] Inventor: Jean-Alain Epinette, 27 rue Lamandin, 62700 Bruay-en-Artois, France

[21] Appl. No.: 6,783

[22] Filed: Jan. 27, 1987

[30] Foreign Application Priority Data

Jan. 27, 1986 [FR] France .............................. 86 01078

[51] Int. Cl.⁴ .............................................. A61F 1/24
[52] U.S. Cl. ........................................ 623/20; 623/18
[58] Field of Search ....................... 623/16, 18, 19, 20, 623/23

[56] References Cited

U.S. PATENT DOCUMENTS

| | | | |
|---|---|---|---|
| 4,038,704 | 8/1977 | Ring | 623/20 |
| 4,055,862 | 11/1977 | Farling | 3/1.91 |
| 4,085,466 | 4/1978 | Goodfellow et al. | 3/1.91 |
| 4,309,778 | 1/1982 | Buechel et al. | 623/20 |
| 4,479,271 | 10/1984 | Bolesky et al. | 623/18 X |

FOREIGN PATENT DOCUMENTS

| | | | |
|---|---|---|---|
| 0010527 | 4/1980 | European Pat. Off. | 623/20 |
| 0032828 | 7/1981 | European Pat. Off. | 623/20 |
| 3429157 | 2/1986 | Fed. Rep. of Germany | 623/20 |
| 2288509 | 5/1976 | France . | |
| 2290883 | 6/1976 | France . | |
| 2338690 | 8/1977 | France . | |
| 2378505 | 8/1978 | France . | |
| 2403068 | 4/1979 | France . | |
| 2575920 | 7/1986 | France | 623/20 |
| 2578162 | 9/1986 | France | 623/19 |
| 2004465 | 4/1979 | United Kingdom . | |
| 0757159 | 8/1980 | U.S.S.R. | 623/20 |

Primary Examiner—Richard J. Apley
Assistant Examiner—David Bender
Attorney, Agent, or Firm—Perry Carvellas

[57] ABSTRACT

A tibial component for a unicompartmental knee prosthesis intended to be fitted without cement, comprises a metal base portion in the general form of a segment of a circular disc with generally flat upper, lower and lateral faces, the latter which is perpendicular to the others extending along the chord of the segment, and a periphery in the form of an arc of a cylinder, the lower and lateral faces being provided to bear against two notch surfaces provided in the plate of the tibia, respectively perpendicular to the general direction of the tibia and parallel thereto along the intercondylar eminence, and a plate member of polymer material which is fixed to the upper face of the base portion and forming a lining for the support of a corresponding condylar component, the base portion having on its lateral face at least one projection arranged to be driven in under the intercondylar eminence, at least one passage for a pinning means to engage into the subjacent bone in the vicinity of its periphery, and on its upper face fixing means for fixing the plate member, which can be used after the base portion has been set in position, and at least a part of the surface of the base portion which is brought into contact with the bone being lined with a covering of porous metal capable of being invaded by the growing spongy bone.

27 Claims, 2 Drawing Sheets

TIBIAL COMPONENT FOR UNICOMPARTMENTAL KNEE PROSTHESIS FOR A CEMENTNESS IMPLANTATION

FIELD OF THE INVENTION

The present invention relates to a tibial component for a unicompartmental knee prosthesis comprising a metal base portion in the general form of a segment of a circular disc with generally flat upper, lower and lateral faces, the latter which is perpendicular to the others extending along the chord of the segment, the lower and lateral faces being provided to bear against two notch surfaces provided in a plate of the tibia respectively perpendicularly to the general direction of the tibia and parallel thereto, along the intercondylar eminence, and a plate member of polymer material which is fixed to the upper face of the base portion and forming a lining for the support of a corresponding condylar component.

BACKGROUND OF THE INVENTION

In the natural pivotal joint of the knee, there are three articular pairs, namely:

an inner femoro-tibial articular pair where the inner femoral condyle slides on the inner tibial plate, an outer femoro-tibial articular pair where the outer femoral condyle slides on the outer tibial plate, a femoro-patellar articular pair where the rear face of the patella slides on the femoral trochlea.

Knee prosthesis can be classified in various categories, depending on the articular pairs replaced:

prostheses which comprise a mechanical articulation joining the femoral and tibial components, which are referred to as constrained or semi-constrained total prostheses;

prostheses which reproduce the contact surfaces of the articular pairs, which are divided into:

prostheses involving replacement of the three articular pairs, referred to as sliding total prostheses;

prostheses involving replacement of an inner or outer femoro-tibial pair, according to the circumstances, referred to as unicompartmental prostheses; and prostheses involving replacement of the femoro-patellar pair, referred to as patella prostheses.

It will be noted moreover that, if the two inner and outer femoro-tibial pairs are to be replaced, the tibial component may be a single one. The present invention relates only to the tibial component of a unicompartmental prosthesis.

The tibial components of unicompartmental prostheses co-operate with a metal condylar component in the form of a crescent with a surface which substantially matches a torus and which is disposed on the prepared condyle by screwing or sealing a lug with an acrylic cement into a cavity provided in the condyle.

The current tibial components of unicompartmental prostheses are composed of a generally flat metal base portion in the form of a segment of a circular disc, with a lower face bearing grooves intended to facilitate engagement of an acrylic cement. A plate of polymer material, typically a high density polyethylene, is provided on the base portion by being moulded thereon. That plate member comprises a flat lateral face which extends a corresponding face of the base portion, extending along the chord of the segment of the circle. After the component has been set in position, the above-mentioned lateral faces bear against a wall surface which is cut into the side of the intercondylar eminence which is disposed between the two tibial plates and to which the crossed ligaments of the knee are attached. As indicated above, preparation of the tibia involves resection of the plate by means of two sawing planes, one being perpendicular to the general direction of the tibia and the other parallel to that direction, extending along the intercondylar eminence, to provide the above-mentioned wall surface.

The component is fixed in the notch caused by resection of the plate, by a cement, generally of acrylic type, the lower face of the base portion resting flat on the sawing plane which is perpendicular to the general direction of the tibia while the lateral face of the component bears against the wall surface cut in the side of the intercondylar eminence.

That type of tibial component suffers from the conventional disadvantages of cemented prostheses, namely the risk of ageing of the polymerised cement which can then crumble away or crack, as well as the risks of deterioration of the bone in contact with the aged acrylic cement, the result being that the tibial component suffers from play. In addition, when setting the prosthesis in position, it is necessary to avoid using an excess of cement in the region adjacent the angle between the sawing planes, such excess being insufficiently squeezed out when the component is forced into the notch and giving rise to the danger of causing vertical mal-alignment of the plate member.

Moreover, if wear of the plate member of the prosthesis requires replacement of the plate member, the entire component has to be removed, the notch surfaces of the tibia have to be re-cut and a new component which is thicker than the first component has to be set in place thereon. Now, the upper epiphysis of the tibia is of an only limited volume, and it is unfortunate to cut into it too deeply.

Tibial components of unicompartmental prostheses which are to be set in position without cement have been proposed. Such prostheses are formed solely by a plate member of polymer material. The plate member is provided with a cylindrical leg with staggered circular fins separated by grooves. The legs can be driven with a force fit into bores provided in the tibial epiphysis in the central part of the sawing plane which is perpendicular to the general direction of the tibia. That type of component also suffers from disadvantages. Setting the component in position requires the sacrifice of a not inconsiderable part of the epiphysis, which makes future replacement of the component a risky proposition. Furthermore, the bore into which the leg of the component is forced is provided in a region where the bony tissue is more in a spongy state than in the corticoidal state and therefore relatively soft, which in not very favourable to a durable hold.

BRIEF DESCRIPTION OF THE INVENTION

The invention therefore proposes a tibial component for a unicompartmental knee prosthesis which is set in position without cement, which requires only a reduced sacrifice of bone in order to provide the mounting notch and in which the plate member of polymer material can be disconnected from the base portion.

For that purpose, the invention proposes a tibial component for a unicompartmental knee prosthesis comprising a metal base portion in the general form of a segment of a circular disc with generally flat upper, lower and lateral faces, the latter which is perpendicular to the others extending along the chord of the segment, and a periphery in the form of an arc of a cylinder, the lower and lateral faces being provided to bear against two notch surfaces provided in the plate of the tibia, respectively perpendicular to the general direction of the tibia and parallel thereto along the intercondylar eminence, and a plate member of polymer material which is fixed to the upper face of the base portion and forming a lining for the support of a corresponding condylar component, the tibial component being intended to be mounted without cement and being characterised in that on its lateral face the base portion has at least one projection arranged to be driven in under the intercondylar eminence, at least one passage for a pinning means to engage into the subjacent bone in the vicinity of its periphery, and on its upper face fixing means for fixing the plate member, which can be used after the base portion has been set in position, and that at least a part of the surface of the base portion which is brought into contact with the bone is lined with a covering of porous metal capable of being invaded by the growing spongy bone.

When setting the prosthesis in place, the base portion is anchored in position by the combination of the projection which is driven under the intercondylar eminence and the pinning means which are engaged into the subjacent bone through the passages which are adjacent to the periphery of the base portion. That immediate primary anchoring effect is completed subsequently by invasion of the covering of porous metal by the growing spongy bone constituting a cementless sealing effect. It will be noted that that type of covering of porous metal was developed to enhance the hold of the cement on articular prostheses, in particular hip prostheses, and was subsequently found to be suitable for being sealed directly by growth of spongy bone, under conditions which are greatly superior to those of conventional cement sealing.

Moreover, the operation of positioning the base portion is not adversely affected by the presence of the plate member which is subsequently fixed thereon. It will be clear that, if wear of the plate member were to appear or if an imperfection in the fit were to become apparent, it would be possible to change the plate member without involving the fixing connection between the base portion and the tibia.

Preferably, the projection on the lateral face is a trapezoidal plate portion which is parallel to the planes of the upper and lower faces, extending in line with the latter, the large base of the plate portion being coincident with the lateral face. That form provides for immediate anchoring with a maximum level of resistance to forces normal to the base portion, which are liable to cause vertical mal-alignments.

Preferably also, the above-mentioned plate portion comprises at least one orifice and the covering of porous metal extends over the whole of the two faces of the plate portion. That arrangement ensures in time that the plate portion is completely sealed in the intercondylar eminence, with the formation of bony bridge portions through the orifices.

Likewise, it is preferred that the whole of the faces of the base portion bearing against the bone should be lined with the covering of porous metal, in order to enjoy the benefit of maximum surface sealing.

In a preferred arrangement, the plate member of the prosthesis has an upper surface with a concavity of large radius, which promotes precise support for the condylar component.

In a preferred arrangement, the means for fixing the plate member of the prosthesis comprise a tenon of dovetail cross-sectional configuration projecting from the upper face of the base portion and extending generally parallel to the lateral face, and a complementary mortise engaged in the plate member. It is preferable for the tenon to be in the shape of a wedge configuration which increases in width from a front end to a rear end, so that engagement of the mortise in parallel relationship to the lateral face causes a wedging action in respect of the tenon. Positional security is further enhanced by providing the base portion with a rim which projects from the upper face in line with the cylindrical periphery and the lateral face. In that way engagement of the plate member into the cavity defined by the rim, by virtue of the elasticity of the polymer material, prevents any movement of the plate member with respect to the base portion under the effect of the stresses of the joint.

It is preferable for a plurality of passages for pinning means to be disposed symmetrically with respect to the mediator plane of the lateral face, so that the bearing effect of the base portion on the prepared subjacent bone is balanced and corresponds to a transmission of the forces through the joint which follows the natural path of the lines of forces.

The pinning means are peferably screws whose heads are embedded in countersinkings in order not to interfere with the plate member bearing against the upper face of the base portion.

BRIEF DESCRIPTION OF THE DRAWINGS

Other features and advantages of the invention will become apparent from the following description which is given by way of example with reference to the accompanying drawings in which.

DETAILED DESCRIPTION OF THE INVENTION

Figure 1:
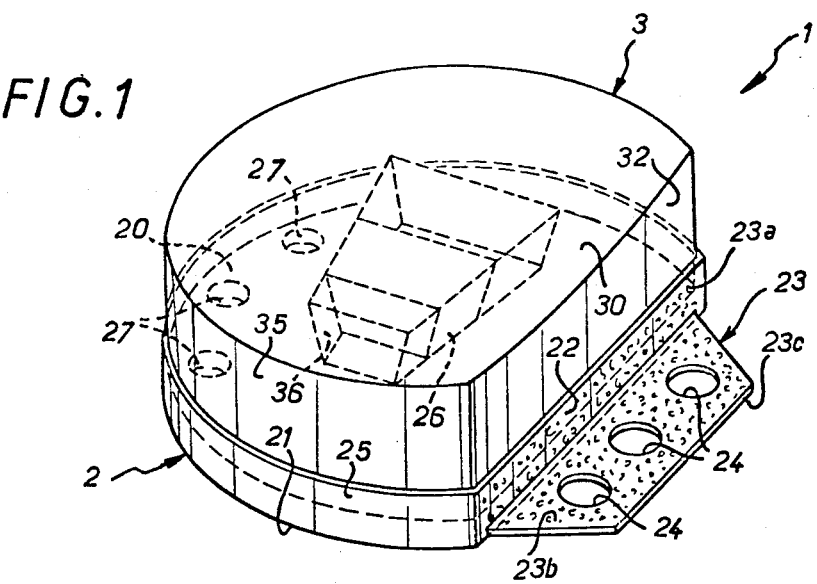
FIG. 1 is a general perspective view of a tibial component of a knee prosthesis according to the invention.
Figure 2:
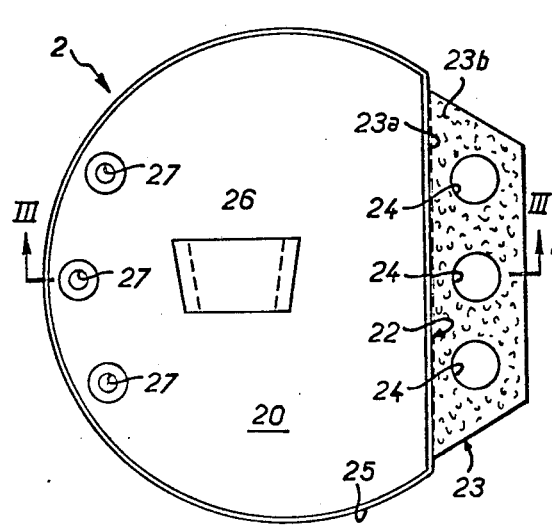
FIG. 2 is a view from above of a tibial component base portion.
Figure 4:
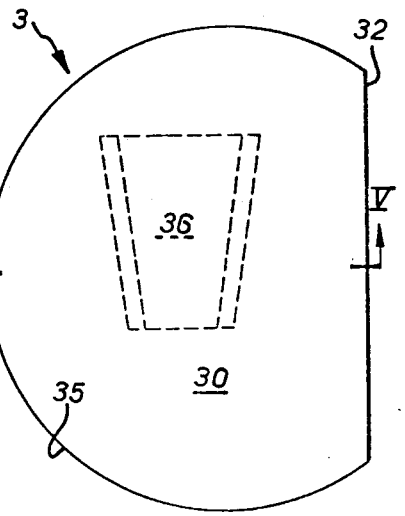
FIG. 4 is a view from above of a tibial component plate member.
Figure 3:
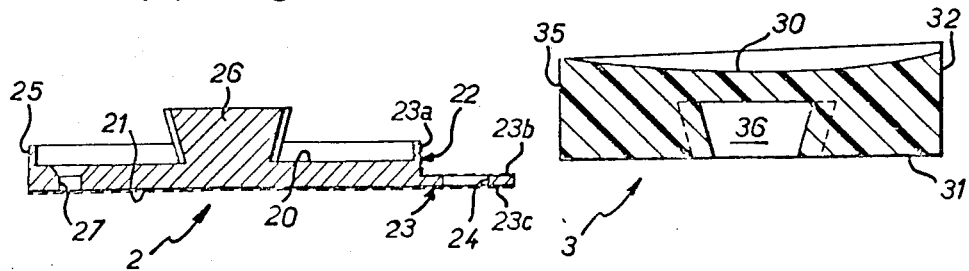
FIG. 3 is a view in section taken along line III—III in FIG. 2.
Figure 5:
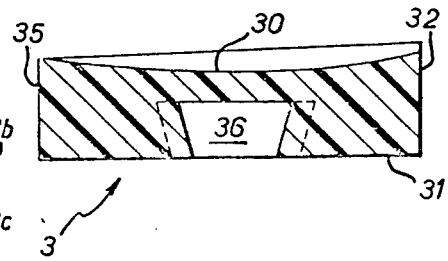
FIG. 5 is a view in section taken along line V—V in FIG. 4.

In the embodiment selected and illustrated in FIGS. 1 through 5, a tibial component 1 generally comprises a metal base portion 2 of stainless steel or titanium TA6V, and a plate member 3 of polymer material, being in this case a high density polyethylene of biocompatible quality, RCH 1000.

The base portion 2 is in the general shape of a segment of a circular disc with an upper face 20, a lower face 21 and a lateral face 22, those three faces being generally flat and the lateral face 22 which extends along the chord of the circular segment being perpendicular to the faces 20 and 21. The upper face 20 is delimited by a rim 25 which extends in alignment with the periphery of the disc and the lateral face 22. A tenon 26 of dovetail configuration projects substantially at the centre of the face 20; the tenon 26 is disposed in a wedge-like configuration in a longitudinal direction parallel to the lateral face 22. Passages 27 are provided in the thickness of the base portion, starting from the face 20 and disposed in the vicinity of the circular periphery of the segment. The passages 27 have a frustoconical countersinking adapted to embed countersunk screw heads. Those passages, of which there are three in this embodiment, are disposed symmetrically with respect to a mediate plane of the lateral face 22, that is to say, one passage is disposed in that plane and the other two passages are symmetrical with respect to that plane.

Projecting from the lateral face 22, a plate portion 23 extends in alignment with the lower face 21. The plate portion 23 is in the form of an isosceles trapezium with its large base 23a coincident with the lateral face 22, and comprises three circular openings 24, the centres of which are aligned in parallel relationship with the bases of the trapezium, at equal spacings from said bases.

The lower face 21, the lateral face 22 and the two faces 23b and 23c of the plate portion 23 are provided with a covering of porous metal formed by particles which are sprayed for example by a plasma torch. That kind of covering which was originally designed to enhance the grip of acrylic cements on the metal components of articular prostheses, has been found to be adapted to be invaded by growing spongy bone and thus, after a post-operative period which is reckoned in weeks, to produce excellent anchoring of metal components to the bones.

The polyethylene plate member 3 is in the general shape of a segment of a disc with a flat lower face 31, a lateral face 32 and a cylindrical periphery 35, which are adapted to be received within the rim 25 with the lower face 31 bearing against the upper face 20 of the base portion.

The upper face 30 is in the form of a concave portion of a sphere, with a large radius of curvature, in order to improve the support for a condylar component, as will be seen hereinafter.

The lower face 31 has a mortise 36 of dovetail configuration, complementary to the tenon 26 on the base portion 2, and which is also of a wedge-like shape in the longitudinal direction. The mortise 36 is so provided that the tenon 26 is locked therein when the plate member 3 is in the position for engaging into the rim 25 and, at the side at which the mortise flares outwardly, it is of a sufficient length for the tenon 26 to engage vertically into the mortise 36, the edges of the tenon passing between the edges of the mortise.

It will be appreciated that, in order to set the plate member 3 in position on the base portion 2, the plate member has to be forced resiliently against the base portion, with the plate member 3 bearing against the rim 25, and that engagement within the rim 25 makes it necessary to insert a blade between the rim 25 and the periphery 35 of the plate member 3 and to push the blade acting as a lever, by lifting the blade.

Moreover, fitting the plate member in position on the base portion results from a sliding movement parallel to the lateral face 22 of the base portion, from the top to the base of the dovetail-like wedge configurations 26 and 36.

Figure 6:
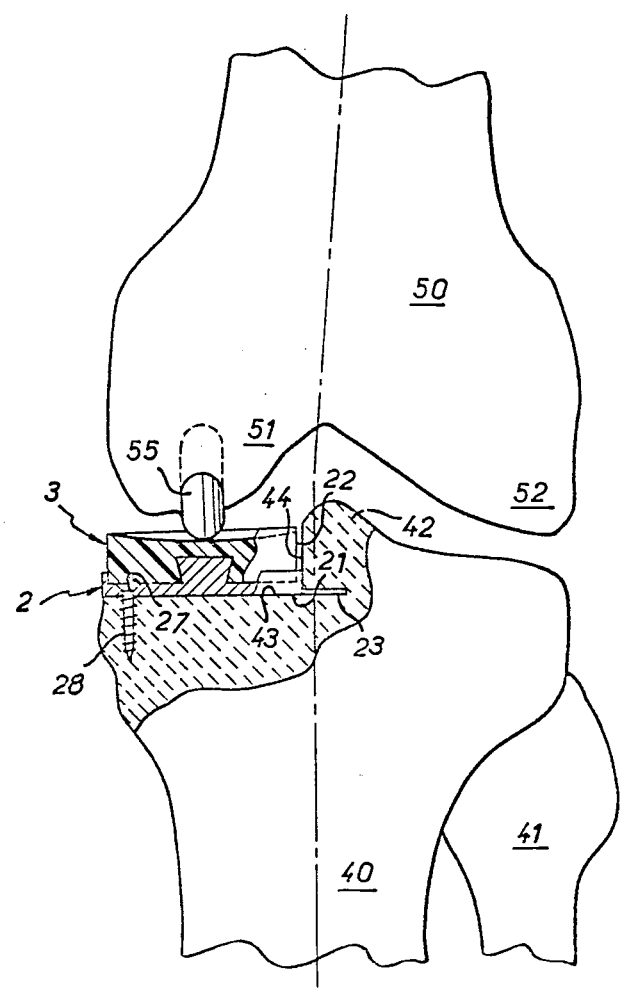
FIG. 6 is a partly sectional diagrammatic view of an inner unicompartmental knee prosthesis comprising a tibial component according to the invention.

In order better to appreciate the reasons why the elements of the tibial component 1 are of the described structures, reference will be made to FIG. 6.

The knee joint which as illustrated is the left joint is shown from the front, with the fitting of an inner unicompartmental prosthesis.

The fibula 41 is pivoted laterally on the tibia 40, on the outward side. Above, the femur 50 terminates with the inner and outer condyles 51 and 52 respectively. Between the condyles is a notch which fits over the intercondylar eminence 42 between the plates of the tibia. The patella is not shown in the drawing; at the illustrated stage of fitting of the prosthesis, the patella is luxated and pushed away in order to clear the joint.

A condylar component 55 has been fitted on to the inner condyle 51, the component 55 being in the form of a fraction of a torus, in such a way as to present a convex surface which is rounded transversely in a gutter-like configuration and perpendicularly to the plane of the drawing, a crescent-like configuration which matches the curvature of the condyle. The rounded edge of the condylar component 55 is to slide on the tibial plate.

Preparation of the tibia, being in this case the left tibia, for fitting a unicompartmental prosthesis, being an inner prosthesis in this case, involves resection of the natural plate by means of two notch planes or surfaces, a notch plane 43 which is perpendicular to the general direction of the tibia (in dash-dotted lines) and the other 44 being parallel to that general direction of the tibia and extending along the intercondylar eminence 42 (and therefore perpendicularly tot he plane of the drawing).

The base portion 2 is placed on the notch plane 43 and pushed laterally (in a direction parallel to the plane of the drawing), forcing the plate portion 23 into the spongy bone beneath the intercondylar eminence 42 until the lateral face 22 of the base portion bears against the notch plane or surface 44.

After that, holes are drilled, through the passages 27, for screws 28 forming pinning means which are then screwed into the bone, parallel to the general direction of the tibia 40, until the heads are embedded in the frustoconical countersinkings while the lower face 21 of the base portion 2 rests properly flat on the cut surface 43.

After that, a plate member 3 of suitable thickness to reconstitute the natural support of the joint is selected and it is fitted on to the tenon, parallel to the cutting plane 44, as already explained above.

It will be appreciated that, from that time, the tibial component is anchored in its definitive location without the risk of a loss of vertical alignment of the component on the tibia. However, that primary anchoring which could possibly deteriorate in the passage of time is consolidated by means of a secondary anchoring effect resulting from invasion of the covering on the lower and lateral faces of the base portion 2 and the two faces of the plate portion 23, that is to say all the surfaces of the base portion which are in contact with the bone, by the growing spongy bone. In addition, growth of the bone will result in the formation, through the openings 24 in the plate portion 23, of bony bridge portions which prevent the plate portion 23 from being torn out.

It will also be appreciated that, if the prosthesis were possibly to show signs of wear (wear of the plate member of high density polyethylene), as the years pass, it is still possible to change the plate member without having to undo the anchoring of the base portion which would have the consequence of sacrificing bone in the plate of the tibia.

It will be appreciated that, if the description sets forth information relating to the method of fitting the tibial components of the invention, that is only in order to bring out the structural particularities of said components and the reason for adopting same. It will be clear that the fitting method is outside the scope of the invention.

It will be appreciated that the invention is not limited to what has been described by way of example and embraces all variations in construction within the scope of the claims.

In particular, the orientation of the short side of the dovetail-section assembly 26–36 will be determined depending on whether the component is left or right, inner or outer, in order for the operation of setting the plate member in position to be effected from the front of the knee (location of the patella), which is the only accessible direction during the operation.

In particular, instead of the tenon 24 being of a wedge-like shape, it could be made in the form of a truncated cone with its axis perpendicular to the upper face 20, being coincident at its small base with the upper face 20.

In addition, although at the present time screws constitute the preferred pinning means, it would be possible to envisage the screws being replaced by pins which are locked in position by expansion, or clips.

What I claim is:

1. A tibial component for a unicompartmental knee prosthesis adapted for cementless implantation, said tibial component comprising a metal base member having an overall configuration comprising a segment of a circular disc including a part cylindrical peripheral portion and a chordal portion,
   said base member having generally flat upper and lower faces and a generally flat lateral face coinciding with the chordal portion and perpendicular to the upper and lower faces, the lower face being adapted to bear against a notch surface in the plate of the tibia generally perpendicular to the longitudinal direction of the tibia and the lateral face being adapted to bear against a notch surface extending parallel to the longitudinal direction of the tibia along the intercondylar eminence,
   a plate member of polymer material having an upper and lower face for forming a lining for supporting a corresponding condylar component,
   means on said base member for fixing said plate member thereto,
   at least one projection from said lateral face adapted to be driven under the intercondylar eminence,
   said base member having at least one passage adjacent to be driven under the intercondylar eminence,
   said base member having at least one passage adjacent its part cylindrical peripheral portion, pinning means being adapted to be received in said passage and to penetrate into subjacent bone,
   at least part of the surface of said base member which is adapted to be brought into contact with bone of the tibia having a porous metal covering adapted to be invaded by spongy bone ingrowth.

2. A tibial component according to claim 1, wherein said projection comprises a plate portion generally parallel to said upper and lower faces of said base member, said plate portion having a lower face in alignment with the first mentioned lower face and at least part of the surface of said plate portion having a porous metal covering adapted to be invaded by spongy bone ingrowth.

3. A tibial component according to claim 2, wherein said plate portion has at least one orifice for bone ingrowth through said plate portion.

4. A tibial component according to claim 3, wherein porous metal covering adapted to be invaded by spongy bone ingrowth extends over substantially the entire surface of said plate portion.

5. A tibial component according to claim 2, wherein said plate portion adjacent said lateral face is substantially coextensive therewith.

6. A tibial component according to claim 1, wherein said covering of a porous metal extends over a substantial portion of the surface of said projection.

7. A tibial component according to claim 2, wherein said plate portion is of trapezoidal configuration and is in alignment with the lower face of said base member, the large base of the trapezoidal configuration adjoining the lateral face of said base member.

8. A tibial component according to claim 2, wherein said porous covering extends over a substantial portion of the surface of said plate portion.

9. A tibial component according to claim 1, wherein said porous covering extends over substantially the entire surface of said base member adapted to come into contact with the bone of the tibia.

10. A tibial component according to claim 1, wherein said plate member has an upper face facing away from said base member having a concave configuration with a large radius of curvature.

11. A tibial component according to claim 1, wherein said means for fixing said plate member permits mounting, removal and replacement of said plate member when said tibial component is implanted.

12. A tibial component according to claim 11, wherein said means for fixing said plate member comprises a tenon of dovetail section projecting from the upper face of said base member and extending generally in a direction parallel to said lateral face, said plate member having in a lower face a mortise complementary in configuration to the tenon, and means for releasing said plate member from said base member.

13. A tibial component according to claim 12, wherein said tenon is of tapered wedge-like shape flaring in said direction parallel to the lateral face, the mortise in said plate member being substantially longer than the tenon in the longitudinal direction to define said means for releasing said plate member from said base member by relative sliding movement.

14. A tibial component according to claim 13, wherein a rim projects upwardly from the upper face of said base member along the cylindrical peripheral portion and said lateral portion of said base member, a lower face of said plate member being adapted to be received inside said rim and retained in place thereby.

15. A tibial component according to claim 1, wherein a rim projects upwardly from the upper face of said base member along the cylindrical peripheral portion and said lateral portion of said base member, a lower face of said plate member being adapted to be received inside said rim and retained in place thereby.

16. A tibial component according to claim 1, wherein said passage is disposed in said base plate remote from said projection.

17. A tibial component according to claim 1, wherein there are a plurality of said passages for a corresponding plurality of pinning means arranged symmetrically relative to a mediate plate of said lateral face.

18. A tibial component according to claim 16, wherein there are a plurality of said passages for a corresponding plurality of pining means arranged symmetrically relative to a mediate plane of said lateral face.

19. A tibial component according to claim 18, wherein said pinning means comprise screws.

20. A tibial component according to claim 1, wherein said screws have heads and said passages have countersinks for receiving the heads of said screws.

21. A tibial component according to claim 1, wherein said pinning means and said projection define primary anchoring means for said tibial component.

22. A tibial component for a unicompartmental knee prosthesis adapted for cementless implantation, said tibial component comprising a metal base member having an overall configuration comprising a segment of a circular disc including a part cylindrical peripheral portion and a chordal portion, said base member having generally flat upper and lower faces and a generally flat lateral face coinciding with chordal portion and perpendicular to the upper and lower faces, the lower face being adapted to bear against a notch surface in the plate of the tibia generally perpendicular to the longitudinal direction of the tibia and the lateral face being adapted to bear against a notch surface extending parallel to the longitudinal direction of the tibia along the intercondylar eminence, a plate member of polymer material having an upper and lower face for forming a lining for supporting the condylar component, said base member having a rim projecting upwardly from its upper face along the cylindrical peripheral portion and lateral portion of said base member, the lower face of said plate member being adapted to be received inside of said rim and retained in place thereby, means on said base member for fixing said plate member thereto, a plate portion projecting from said lateral face adapted to be driven under the intercondylar eminence, said plate portion having an upper and lower face and being generally parallel to the upper and lower faces of said base member and having at least one orifice therethrough for bone ingrowth through said plate portion, said base member having at least one passage adjacent its part cylindrical peripheral portion, pinning means being adapted to be received in said passage and to penetrate into subjacent bone, the surface of said base member which is adapted to be brought into contact with bone of the tibia and the surface of said plate portion having a porous metal covering adapted to be invaded by spongy bone ingrowth.

23. A tibial component according to claim 22, wherein the means for fixing the plate member on the base member permits mounting, removal and replacement of said plate member when said tibial component is implanted which comprises a tenon of dovetail section projecting from the upper face of said base member and extending generally in a direction parallel to said lateral face, said plate member having in said lower face a mortise complimentary in configuration to the tenon.

24. A tibial component according to claim 23 wherein said tenon is of tapered wedge-like shape flaring in said direction parallel to the lateral face, the mortise in said plate member being substantially longer than said tenon in the longitudinal direction to define said means for releasing said plate member from said base member by relative sliding movement.

25. A tibial component according to claim 22, wherein said plate portion is of trapezoidal configuration and is in alignment with the lower face of said base member, the large base of the trapezoidal configuration adjoining said lateral face and being substantially coextensive therewith.

26. A tibial component according to claim 22 wherein said porous metal covering extends substantially over the entire surface of said base member adapted to come into contact with the bone of the tibia and extends substantially over the entire surface of said plate portion.

27. A tibial component according to claim 22 wherein there are disposed in said base member remote from said projection a plurality of said passages for a corresponding plurality of pinning means arranged symmetrically relative to a mediate plane of said lateral face, said pinning means comprise screws and said screws have heads and said passages have countersinks for receiving the heads of the screws.

* * * * *

UNITED STATES PATENT AND TRADEMARK OFFICE
CERTIFICATE OF CORRECTION

PATENT NO. : 4,743,261
DATED : May 10, 1988
INVENTOR(S) : Jean-Alain Epinette

It is certified that error appears in the above-identified patent and that said Letters Patent is hereby corrected as shown below:

Column 7, delete lines 54 and 55 in their entirety.

Signed and Sealed this

Twenty-seventh Day of September, 1988

*Attest:*

DONALD J. QUIGG

*Attesting Officer*　　　　　*Commissioner of Patents and Trademarks*